United States Patent [19]

Diehr

[11] Patent Number: 5,162,539
[45] Date of Patent: Nov. 10, 1992

[54] PREPARATION OF 2-ALKYLTHIO-1,3,4-THIADIAZOLES

[75] Inventor: Hans-Joachim Diehr, Wuppertal, Fed. Rep. of Germany

[73] Assignee: Bayer Aktiengesellschaft, Leverkusen, Fed. Rep. of Germany

[21] Appl. No.: 646,563

[22] Filed: Jan. 25, 1991

[30] Foreign Application Priority Data

Feb. 6, 1990 [DE] Fed. Rep. of Germany ....... 4003436

[51] Int. Cl.$^5$ ........................................... C07D 285/12
[52] U.S. Cl. .................................................. 548/136
[58] Field of Search ......................................... 540/136

[56] References Cited

U.S. PATENT DOCUMENTS

| | | | |
|---|---|---|---|
| 3,562,284 | 2/1971 | Newman et al. | 548/136 |
| 4,791,208 | 12/1988 | Forster | 548/136 |
| 4,988,378 | 1/1991 | Forster | 548/136 |
| 4,988,380 | 1/1991 | Forster | 548/136 |

FOREIGN PATENT DOCUMENTS

| | | |
|---|---|---|
| 0148501 | 7/1985 | European Pat. Off. . |
| 0165537 | 12/1985 | European Pat. Off. . |
| 0348734 | 1/1990 | European Pat. Off. . |
| 0348736 | 1/1990 | European Pat. Off. . |
| 3722320 | 1/1989 | Fed. Rep. of Germany . |
| 3422861 | 1/1990 | Fed. Rep. of Germany . |

OTHER PUBLICATIONS

Justus Liebigs Annalen Der Chemie, Band 660, Dec. 31, 1962, pp. 144–146.

W. Theilheimer: "Synthetic methods of organic chemistry", No. 16, 1962, p. 218.
Handbook of Houben-Weyl, vol. 8 (1952), pp. 466–467.

Primary Examiner—Robert Gerstl
Attorney, Agent, or Firm—Sprung Horn Kramer & Woods

[57] ABSTRACT

A process for the preparation of a 2-alkylthio-1,3,4-thiadiazole of the formula

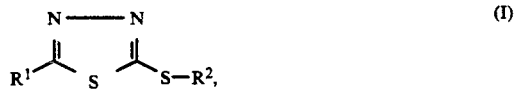

in which
R$^1$ represents alkyl which is optionally substituted by halogen and
R$^2$ represents alkyl or aralkyl, which comprises reacting a carboxylic acid of the formula $$R^1\text{—COOH} \qquad (II),$$

with a dithiocarbazic ester of the formula

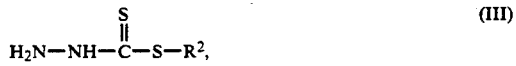

in the presence of phosphoryl chloride (POCl$_3$) at a temperature between −20° C. and +120° C.

9 Claims, No Drawings

PREPARATION OF 2-ALKYLTHIO-1,3,4-THIADIAZOLES

The invention relates to a new process for the preparation of 2-alkylthio-1,3,4-thiadiazoles, which can be used as intermediates for the preparation of plant protection agents.

It has been disclosed that certain 2-alkylthio-5-halogenoalkyl-1,3,4-thiadiazoles such as, for example, 2-methylthio-5-trifluoromethyl-1,3,4-thiadiazole, are obtained when methyl dithiocarbazate is reacted with corresponding carboxylic anhydrides such as, for example, trifluoroacetic anhydride (cf. U.S. Pat. No. 3,562,284), or with corresponding carboxylic acids such as, for example, trifluoroacetic acid, in a solvent such as toluene, in the presence of phosphorus trichloride and pyridine, with the addition of concentrated sulphuric acid (cf. DE-A-3,422,861), or with corresponding carbonyl chlorides such as, for example, trifluoroacetyl chloride, in a solvent such as diethylene glycol dimethyl ether, likewise in the presence of pyridine and with the addition of concentrated sulphuric acid (cf. DE-A-3,722,320).

The first-mentioned synthesis method is little suited for application on an industrial scale for financial reasons, since relatively expensive carboxylic anhydrides are used in excess. The reaction with carboxylic acids, phosphorus trichloride, pyridine and sulphuric acid, as well as the reaction with carbonyl chlorides, pyridine and sulphuric acid, requires a working-up process in which the pyridine is separated off after the reaction and, if appropriate, recovered. Moreover, phosphorus trichloride forms sparingly soluble products in the reaction, which make mixing difficult. Also, the yields to be achieved in the known synthesis methods are not entirely satisfactory.

It has now been found that 2-alkylthio-1,3,4-thiadiazoles of the general formula (I)

(I)

in which
R$^1$ represents alkyl which is optionally substituted by halogen and
R$^2$ represents alkyl or aralkyl,
are obtained in very good yields and in high purity when carboxylic acids of the general formula (II)

(II), in which
R$^1$ has the abovementioned meaning,
are reacted with dithiocarbazic esters of the general formula (III)

(III)

in which
R$^2$ has the abovementioned meaning,
in the presence of phosphoryl chloride (POCl$_3$) at temperatures between $-20°$ C. and $+120°$ C.

Surprisingly, the process according to the invention, in which only phosphoryl chloride is employed instead of the combination of phosphorus trichloride/pyridine, makes it possible to prepare the 2-alkylthio-1,3,4-thiadiazoles of the formula (I), without exception, in better yields than by the above-mentioned, known processes, neither the use of an additional solvent or diluent nor the addition of sulphuric acid being necessary.

Accordingly, the advantages of the process according to the invention are mainly that it is more cost-effective with regard to the reactants and less complicated with regard to the reaction and working-up, compared with the known processes.

The process according to the invention preferably relates to the preparation of 2-alkylthio-1,3,4-thiadiazoles of the formula (I) in which
R$^1$ represents C$_1$-C$_4$-alkyl which is optionally substituted by fluorine, chlorine and/or bromine and
R$^2$ represents C$_1$-C$_4$-alkyl or benzyl.

In particular, the process according to the invention relates to the preparation of compounds of the formula (I) in which
R$^1$ represents methyl which is monosubstituted to trisubstituted by fluorine and/or chlorine and
R$^2$ represents methyl.

If, for example, trifluoroacetic acid and methyl dithiocarbazate are used as starting substances, the course of the reaction in the process according to the invention can be outlined by the following equation:

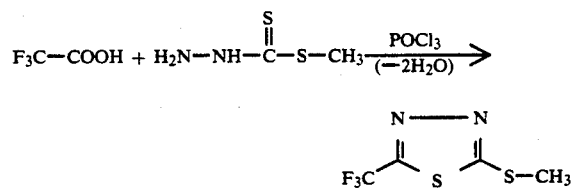

Formula (II) provides a general definition of the carboxylic acids to be used as starting substances in the process according to the invention. In formula (II), R$^1$ preferably, or in particular, has the meaning which has already been indicated above in connection with the description of the compounds of the formula (I) to be prepared according to the invention, as being preferred, or particularly preferred, for R$^1$.

Examples of the starting substances of the formula (II) which may be mentioned are: fluoroacetic acid, difluoroacetic acid, trifluoroacetic acid, chloroacetic acid, dichloroacetic acid, trichloroacetic acid, chlorodifluoroacetic acid and fluorodichloroacetic acid.

The starting substances of the formula (II) are known chemicals for organic synthesis.

Formula (III) provides a general definition of the dithiocarbazic esters furthermore to be used as starting substances in the process according to the invention. In formula (III), R$^2$ preferably, or in particular, has the meaning which has already been indicated above in connection with the description of the compounds of the formula (I) to be prepared according to the invention, as being preferred, or particularly preferred, for R$^2$.

Examples of the starting substances of the formula (III) which may be mentioned are: methyl dithiocarbazate, ethyl dithiocarbazate and benzyl dithiocarbazate.

The starting substances of the formula (III) are known (cf., for example, DE-A-1,934,809 and DE-A-3,709,414).

When carrying out the process according to the invention, the reaction temperatures can be varied within a substantial range. In general, the process is carried out at temperatures between −20° C. and +120° C., preferably at temperatures between 0° C. and +90° C.

The process according to the invention is generally carried out under atmospheric pressure. However, it is also possible to carry out the process under increased or reduced pressure, generally between 0.1 and 10 bar.

For carrying out the process according to the invention, between 0.8 and 1.2 moles, preferably between 0.95 and 1.05 moles, of dithiocarbazic ester of the formula (III) and between 1 and 10 moles, preferably between 1.5 and 5 moles, of phosphoryl chloride are generally employed per mole of carboxylic acid of the formula (II).

The reactants can be combined in any desired sequence.

In a preferred embodiment of the process according to the invention, the carboxylic acid of the formula (II) and the dithiocarbazic ester of the formula (III) are initially introduced, and the phosphoryl chloride is slowly metered in with stirring.

In another preferred variant of the process according to the invention, the carboxylic acid of the formula (II) is first mixed with the phosphoryl chloride, and the dithiocarbazic ester of the formula (III) is slowly metered in with stirring.

In both variants, the reaction mixture is then stirred until the reaction is complete, preferably at elevated temperature, and the mixture is then concentrated under reduced pressure. The residue is worked up by customary methods. For example, it is stirred with ice-water; if appropriate, the mixture is rendered nearly neutral; the mixture is shaken with an organic solvent which is virtually immiscible with water such as, for example, toluene or chloroform, the organic phase is separated off and, if appropriate, washed until nearly neutral, and, if appropriate, dried and filtered. The solvent is carefully distilled off from the filtrate under reduced pressure. The residue which remains essentially contains the product of the formula (I) which, in general, needs no further purification before further processing.

The 2-alkylthio-1,3,4-thiadiazoles to be prepared by the process according to the invention can be used as microbicides (cf. U.S. Pat. No. 3,562,284, DE-A-3,422,861 and DE-A-3,722,320).

PREPARATION EXAMPLES

Example 1

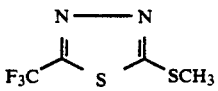

To 30.5 g (0.25 mol) of methyl dithiocarbazate there are added 28.5 g (0.25 mol) of trifluoroacetic acid. To this mixture there are then added dropwise 84 g (0.55 mol) of phosphoryl chloride, with stirring and cooling, during which process the internal temperature is maintained below 45° C. The reaction mixture is then heated slowly—within 3 hours—to an internal temperature of 80° C. (evolution of gas!). When the evolution of gas has ceased, the mixture is concentrated under reduced pressure, the residue is stirred with ice-water, a pH of 6 is established using 2N sodium hydroxide solution, and the product is extracted with 150 ml of toluene. The solution in toluene is washed with 5 % strength sodium hydrogen carbonate solution and then with water; the solvent is then carefully distilled off under a water pump vacuum at 50° C. (bath temperature).

This gives 62 g of a yellow oil which, according to analysis by gas chromatography, contains 75 % of 2-methylthio-5-trifluoromethyl-1,3,4-thiadiazole (remainder: toluene); yield: 93 % of theory.

Example 1a

The compound of Example 1 can also be prepared as follows:

To a mixture of 100 ml of phosphoryl chloride and 57 g (0.5 mol) of trifluoroacetic acid there are added portionwise—within half an hour—61 g (0.5 mol) of methyl dithiocarbazate, with stirring and cooling by ice-water. The reaction mixture is then stirred for 15 minutes without cooling and is then heated slowly to an internal temperature of 80° C. (evolution of gas) and stirred at this temperature until the evolution of gas has ceased. Thereafter the reaction mixture is concentrated under reduced pressure, and the residue is stirred with toluene/ice-water; then the organic phase is separated, washed with water and concentrated again under reduced pressure.

This gives 96.5 g of a yellow oil which, according to analysis by gas chromatography, contains 98.5% of 2-methylthio-5-trifluoromethyl-1,3,4-thiadiazole; yield: 95% of theory.

The compounds of the formula (I)

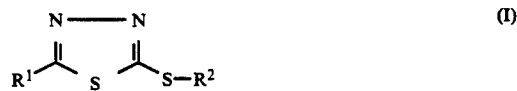

which are listed in Table 1 below can, for example also be prepared analogously to Example 1 and following the general description of the process according to the invention

TABLE 1

| Example No. | R¹ | R² | Boiling point/ pressure (°C./mbar) (or: melting point m.p.) | Yield (% of theory) |
| --- | --- | --- | --- | --- |
| 2 | ClF₂C— | CH₃ | 120/20 | 89 |
| 3 | FCl₂C— | CH₃ | 96–97/2 | |
| 4 | Cl₃C— | CH₃ | (m.p.: 31° C.) | |
| 5 | F₂CH— | CH₃ | 73–74/1 | |
| 6 | Cl₂CH— | CH₃ | 112/1 | |
| 7 | ClCH₂— | CH₃ | (m.p.: 68° C.) | |
| 8 | H₃C— | CH₃ | 88–89/1 | |

It will be understood that the specification and examples are illustrative but not limitative of the present invention and that other embodiments within the spirit and scope of the invention will suggest themselves to those skilled in the art.

I claim;

1. A process for the preparation of a 2-alkylthio-1,3,4-thiadiazole of the formula

in which

R¹ represents alkyl which is optionally substituted by halogen and

R² represents alkyl or aralkyl, which consists essentially of reacting a carboxylic acid of the formula $$R^1\text{—COOH} \qquad (II),$$

with a dithiocarbazic ester of the formula $$H_2N\text{—NH}\text{—}\overset{\underset{\|}{S}}{C}\text{—S—}R^2, \qquad (III)$$

in the presence of phosphoryl chloride (POCl₃) at a temperature between −20° C. and +120° C.

2. The process according to claim 1, wherein the temperature is between 0° and +90° C.

3. The process according to claim 1, wherein 0.8 to 1.2 moles of dithiocarbazic ester are employed per mole of carboxylic acid.

4. The process according to claim 1, wherein 1 to 10 moles of phosphoryl chloride are employed per mole of carboxylic acid.

5. The process according to claim 1, in which R¹ represents C₁-C₄-alkyl which is optionally substituted by at least one of fluorine, chlorine and bromine.

6. The process according to claim 1, in which R¹ represents methyl which is monosubstituted to trisubstituted by at least one of fluorine and chlorine.

7. The process according to claim 1, in which R² represents C₁-C₄-alkyl or benzyl.

8. The process according to claim 1, in which R² represents methyl.

9. The process according to claim 1, wherein 0.95 to 1.05 moles of dithiocarbazic ester are employed per mole of carboxylic acid, 1.5 to 5 moles of phosphoryl chloride are employed per mole of carboxylic acid, and in which R¹ represents methyl which is monosubstituted to trisubstituted by at least one of fluorine and chlorine, and R² represents methyl.

* * * * *